(12) United States Patent
Li et al.

(10) Patent No.: US 8,430,920 B2
(45) Date of Patent: Apr. 30, 2013

(54) DEVICE AND METHODS FOR TREATMENT OF TISSUE

(76) Inventors: Kasey K. Li, Palo Atlo, CA (US); George Y. Choi, Atherton, CA (US)

(*) Notice: Subject to any disclaimer, the term of this patent is extended or adjusted under 35 U.S.C. 154(b) by 0 days.

(21) Appl. No.: 12/167,214

(22) Filed: Jul. 2, 2008

(65) Prior Publication Data

US 2009/0124958 A1    May 14, 2009

Related U.S. Application Data

(60) Provisional application No. 60/976,177, filed on Sep. 28, 2007, provisional application No. 61/058,507, filed on Jun. 3, 2008.

(51) Int. Cl.
*A61N 5/067*    (2006.01)
(52) U.S. Cl.
USPC .............................................. 607/89; 607/88
(58) Field of Classification Search .................. 128/898; 606/2–50
See application file for complete search history.

(56) References Cited

U.S. PATENT DOCUMENTS

| | | | |
|---|---|---|---|
| 4,016,870 A * | 4/1977 | Lock ............................ | 600/548 |
| 4,564,011 A | 1/1986 | Goldman | |
| 4,578,061 A | 3/1986 | Lemelson | |
| 4,900,303 A | 2/1990 | Lemelson | |
| 5,169,396 A | 12/1992 | Dowlatshahi et al. | |
| 5,222,953 A | 6/1993 | Dowlatshahi | |
| 5,250,068 A | 10/1993 | Ideguchi et al. | |
| 5,306,274 A | 4/1994 | Long | |
| 5,728,094 A | 3/1998 | Edwards | |
| 5,746,224 A | 5/1998 | Edwards | |
| 5,792,140 A | 8/1998 | Tu et al. | |
| 5,800,429 A | 9/1998 | Edwards | |
| 5,807,385 A | 9/1998 | Keller | |
| 5,817,049 A | 10/1998 | Edwards | |
| 5,823,197 A | 10/1998 | Edwards | |
| 5,827,277 A | 10/1998 | Edwards | |
| 5,836,938 A | 11/1998 | Slatkine | |
| 5,843,077 A | 12/1998 | Edwards | |
| 5,916,150 A | 6/1999 | Sillman | |

(Continued)

FOREIGN PATENT DOCUMENTS

| | | |
|---|---|---|
| EP | 0815798 A | 1/1998 |
| WO | WO 92/10142 | 6/1992 |

(Continued)

OTHER PUBLICATIONS

Arakane, K. et al, "Singlet oxygen (1 delta g) generation from coproporphyrin in Propionibacterium acnes on irradiation," *Biochem Biophys Res Commun*, vol. 223, pp. 578-582, 1996.

(Continued)

*Primary Examiner* — Bill Thomson
*Assistant Examiner* — Jeffrey Lipitz
(74) *Attorney, Agent, or Firm* — Levine Bagade Han LLP

(57) ABSTRACT

A device and methods for treating tissue via laser energy to induce tissue reduction and/or necrosis are described herein. Laser energy may be applied to a tissue region via an optical fiber advanced through a lumen of at least one needle. Fluid may also be infused or injected into the tissue region through at least one needle. Tissue reduction and/or necrosis of a target tissue region in turn reduces the appearance of droopy, baggy and/or wrinkled skin.

14 Claims, 16 Drawing Sheets

U.S. PATENT DOCUMENTS

| | | | |
|---|---|---|---|
| 5,954,710 | A | 9/1999 | Paolini et al. |
| 5,979,453 | A | 11/1999 | Savage et al. |
| 5,984,915 | A | 11/1999 | Loeb et al. |
| 6,039,729 | A | 3/2000 | Durville et al. |
| RE36,903 | E | 10/2000 | Keller |
| 6,176,854 | B1 | 1/2001 | Cone |
| 6,200,313 | B1 | 3/2001 | Abe et al. |
| 6,200,332 | B1 | 3/2001 | Del Giglio |
| 6,206,873 | B1 | 3/2001 | Paolini et al. |
| 6,277,116 | B1 | 8/2001 | Utely et al. |
| 6,355,054 | B1 | 3/2002 | Neuberger |
| 6,361,531 | B1 | 3/2002 | Hissong |
| 6,402,739 | B1 | 6/2002 | Neev |
| 6,409,720 | B1 | 6/2002 | Hissong et al. |
| 6,454,763 | B1 | 9/2002 | Motter et al. |
| 6,517,535 | B2 | 2/2003 | Edwards |
| 6,605,079 | B2 | 8/2003 | Shanks et al. |
| 6,692,494 | B1 | 2/2004 | Cooper et al. |
| 6,706,016 | B2 | 3/2004 | Cory et al. |
| 6,740,082 | B2 | 5/2004 | Shadduck |
| 6,770,070 | B1 | 8/2004 | Balbierz |
| 6,802,838 | B2 | 10/2004 | Loeb et al. |
| 2002/0026188 | A1* | 2/2002 | Balbierz et al. ............. 606/41 |
| 2002/0151879 | A1 | 10/2002 | Loeb |
| 2002/0193781 | A1 | 12/2002 | Loeb |
| 2003/0120269 | A1* | 6/2003 | Bessette et al. ............. 606/32 |
| 2004/0044337 | A1* | 3/2004 | Shafirstein et al. ......... 606/28 |
| 2005/0049582 | A1 | 3/2005 | DeBenedictis et al. |
| 2005/0240147 | A1 | 10/2005 | Makower et al. |
| 2006/0095066 | A1 | 5/2006 | Chang et al. |
| 2006/0148737 | A1* | 7/2006 | Harmon ..................... 514/44 |
| 2006/0253112 | A1 | 11/2006 | Suarez et al. |
| 2006/0276861 | A1 | 12/2006 | Lin |
| 2007/0060989 | A1 | 3/2007 | Deem et al. |
| 2007/0142885 | A1 | 6/2007 | Hantash et al. |
| 2007/0219540 | A1 | 9/2007 | Masotti et al. |
| 2007/0244529 | A1 | 10/2007 | Choi et al. |
| 2008/0027423 | A1 | 1/2008 | Choi et al. |
| 2008/0027520 | A1 | 1/2008 | Choi et al. |
| 2008/0077198 | A1* | 3/2008 | Webb et al. ................. 607/88 |
| 2010/0010334 | A1* | 1/2010 | Bleich et al. ............... 600/373 |

FOREIGN PATENT DOCUMENTS

| | | |
|---|---|---|
| WO | WO 93/15664 | 8/1993 |
| WO | WO 01/22897 | 4/2001 |
| WO | WO 2006/121734 | 11/2006 |
| WO | WO2006121734 | 11/2006 |
| WO | WO 2008/014064 | 1/2008 |
| WO | WO 2008/014046 | 11/2008 |
| WO | WO 2009/042268 | 4/2009 |

OTHER PUBLICATIONS

European Patent Application No. 07797626.4 filed May 21, 2007 in the name of Choi et al., Office Action mailed Dec. 29, 2009.

European Patent Application No. 07797626.4 filed May 21, 2007 in the name of Choi et al., Supplementary European Search Report mailed Sep. 14, 2009.

European Patent Application No. 07798709.7 filed Jun. 18, 2007 in the name of Choi et al., Supplementary European Search Report mailed Sep. 14, 2009.

Futsaether, CM, et al, "Intracellular pH changes induced in Propionibacterium acnes by UVA radiation and blue light," *J Photochem Photobiol B*, vol. 31, pp. 125-131, 1995.

PCT International Patent Application No. PCT/US2007/069384 filed May 21, 2007 in the name of Costa, International Preliminary Report on Patentability mailed Feb. 5, 2009.

PCT International Patent Application No. PCT/US2007/069384 filed May 21, 2007 in the name of Costa, International Search Report and Written Opinion mailed Sep. 11, 2008.

PCT International Patent Application No. PCT/US2007/071478 filed Jun. 18, 2007 in the name of Costa, International Search Report and Written Opinion mailed May 15, 2008.

PCT International Patent Application No. PCT/US2007/071478 filed Jun. 18, 2007 in the name of Costa, International Preliminary Report on Patentability mailed Feb. 5, 2009.

PCT International Patent Application No. PCT/US2008/069105 filed Jul. 2, 2008 in the name of Choi et al., International Preliminary Report on Patentability mailed Apr. 8, 2010.

PCT International Patent Application No. PCT/US2008/069105 filed Jul. 2, 2008 in the name of Choi et al., International Search Report and Written Opinion mailed Oct. 22, 2008.

Taylor, Barry L. et al, "Electron Acceptor Taxis and Blue Light Effect on Bacterial Chemotaxis," *Journal of Bacteriology*, vol. 40:2, pp. 567-573, Nov. 1979.

U.S. Appl. No. 11/697,172, filed Apr. 5, 2007 in the name of Choi et al., Final Office Action mailed Apr. 17, 2009.

U.S. Appl. No. 11/697,172, filed Apr. 5, 2007 in the name of Choi et al., Non-final Office Action mailed May 1, 2008.

U.S. Appl. No. 11/697,172, filed Apr. 5, 2007 in the name of Choi et al., Non-final Office Action mailed Oct. 27, 2009.

U.S. Appl. No. 11/750,873, filed May 18, 2007 in the name of Choi et al., Final Office Action mailed Jun. 25, 2009.

U.S. Appl. No. 11/750,873, filed May 18, 2007 in the name of Choi et al., Non-final Office Action mailed Sep. 19, 2008.

* cited by examiner

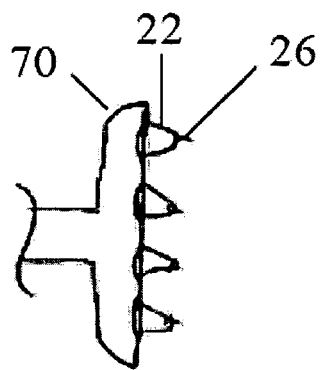
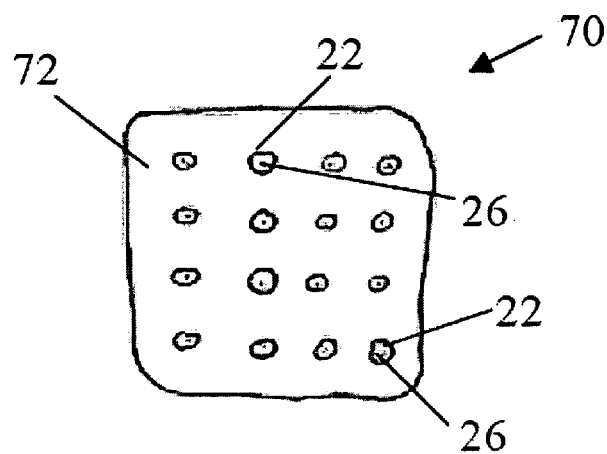
Fig. 9     Fig. 10
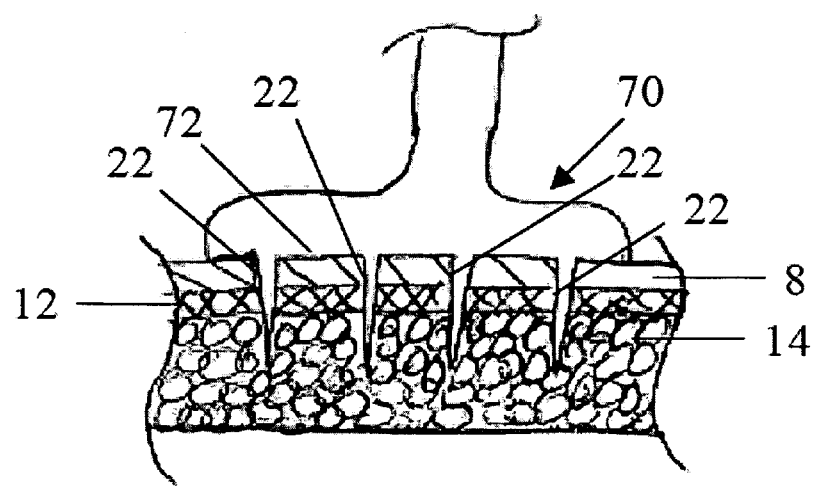
Fig. 11

DEVICE AND METHODS FOR TREATMENT OF TISSUE

CROSS-REFERENCE TO RELATED APPLICATIONS

This application claims the benefits of priority to U.S. Prov. Pat. Apps. 60/976,177 filed Sep. 28, 2007 and 61/058,507 filed Jun. 3, 2008, each of which is incorporated herein by reference in its entirety.

FIELD OF THE INVENTION

The present invention relates to device and methods for treating tissue of a patient. More particularly, the present invention relates to device and methods for altering the appearance of a tissue region such as the facial region, e.g. eyelids, jowls, neck, etc., by reducing baggy and/or wrinkled skin by applying ablation energy to the tissue, such as fat, muscle, dermis, etc., to result in tissue shrinkage and/or necrosis leading to reduction of bags and/or wrinkles.

BACKGROUND OF THE INVENTION

Skin and underlying tissues typically have a flat and toned appearance in youth. Over time, age-related loss of elasticity and other factors, such as heredity, sun damage, obesity, and normal wear and tear, may contribute to changes in the skin, muscle, fat, and support system which may result in the appearance of baggy and/or wrinkled skin. Many turn to cosmetic surgery to reduce the signs of aging, particularly in the facial region. For example, lower eyelid "bags", or blepharaochalasis, is a very common condition seen with normal aging, fatigue, allergies, swelling, obesity, etc. Eyelid skin doesn't have fat of its own, but instead the fat located in the eyelid area is from orbital fat. The facial eyelid muscles and skin hold this orbital fat in place resulting in a youthful line starting from the eyelashes to the cheek. With time, under eye bags may result from the fat putting pressure on lax muscle, ligament, and skin wall. Baggy eyelids may also result from an extra amount of orbital fat.

Eyelid fat may not be removed by liposuction since the tissues surrounding the eyes are too delicate. However, there are other surgical options (both internal and external surgical procedures), such as blepharoplasty, which involves removing lower eyelid fat through an incision on the back of the eyelid. However skin resurfacing with a chemical peel or carbon dioxide laser may also be performed to remove wrinkles and/or excess skin.

Reduction of tissue regions such as eyelid fat may be accomplished by the application of ablation instruments such as lasers. However, conventional laser instruments because of their size typically require the introduction of the instrument through surgical incisions made through the skin to obtain access to the tissue regions to be ablated. Thus, although laser instrumentation may be effective in ablating subcutaneous tissue regions, access to these tissue regions may nonetheless require surgical incisions along with the accompanying bleeding and pain associated with such procedures.

In addition to baggy lower eyelids, the upper eyelid may also have a baggy or droopy appearance. Upper eye bags may also be caused by orbital fat, extra skin (dermochalasis), brow ptosis, or any combination. Most commonly, dermatochalasis presents a cosmetic concern only, with patients complaining of droopy eyelids. However, some patients may complain of true functional difficulties, such as obstruction of the superior visual field. Belpharoplasty or a brow lift may be performed to reduce upper eyelid bulges and/or wrinkles.

Another area of facial aging may be seen in the mouth and chin area. Below the mouth, the chin may become prominent as the area surrounding the chin shows volume depletion. This, combined with the gravitational movement of the cheek's fat pad (malar fat pad), creates unattractive jowls.

The neck may also be an area where the signs of aging are apparent. Weakened or loose neck muscles may result in the appearance of neck bands, which is sometimes commonly referred to as a "turkey wattle." Platysmaplasty is a common surgical technique used to correct sagging skin in the neck area. Incisions under the chin and/or behind the ears are made to access the platysma (neck muscle) and manipulate it accordingly. Sometimes, the muscle may even be removed. An endoscope may be used during surgery which may result in a smaller incision.

In order to have a more youthful appearance many times people turn to cosmetic surgery to correct the sagging aspects of the face. Surgery may sometimes need to be repeated to obtain the desired look which may lead to excess scarring. There are other non-surgical procedures for correcting wrinkles such as laser resurfacing, deep acid peels and Botox injections. As many are all aware, these aggressive procedures carry risks. Also, they can often have long recovery times and leave a person with an unnatural appearance. Therefore, there is a need for a less invasive procedure which is more precise and has a shorter recovery time.

BRIEF SUMMARY OF THE INVENTION

Inducing tissue reduction and/or necrosis in target tissue regions such as fat, muscle, and/or nerves, particularly in the eye, cheek, and neck area of a patient, may reduce the appearance of bagginess and/or wrinkles. Tissue reduction and/or necrosis in other tissue regions, such as the soft palate, tongue, and later pharyngeal walls may also result in increasing the stiffness of the tissue to alter its vibrating characteristics and/or to prevent or inhibit collapse of the tissue to prevent obstruction of an airway.

One method for inducing tissue reduction and/or necrosis is to apply laser energy to the target tissue region using a device comprising an elongated shaft having a distal end, a proximal end, and a length there between. The proximal end may have a handle assembly and the distal end may contain at least one piercing tip, such as a needle. Although piercing tip and needle are used interchangeably herein, needle is also intended to encompass any suitable tissue piercing instrument which may be utilized as described herein. The distal end may also contain multiple needles to treat a larger range of tissue. A larger range of tissue may also be treated by inserting the needle through a single insertion site at a plurality of angles relative to the tissue region. Each needle may have between a 20 and 30 gauge diameter, or smaller, to avoid having to create an incision and loss of blood when inserted through the patient's skin into the target tissue region. If multiple needles are used, the needle gauge may be the same or different gauges as the other needles.

At least one optical fiber may be positioned within or along the needle such that a distal end of the optical fiber is movable with respect to the needle so that the terminal end of the optical fiber may extend beyond the needle into the target tissue region. In order to apply laser energy through the optical fiber, a laser generator may be provided which is in optical communication with a proximal end of the optical fiber or fibers.

The diameter of the piercing needle tip is particularly advantageous in having a size, for example, 20 to 30 gauge or smaller, which is sufficiently small such that it may be inserted into and through the patient's skin without causing any bleeding or requiring any surgical incision or intervention. Access to the subcutaneous tissue may accordingly be provided by advancing the piercing tip directly into the tissue region and into the subcutaneous tissue to be treated. The optical fiber, which is also particularly small in diameter to be advanced through the needle, may be utilized to deliver the laser energy into the subcutaneous tissue, whereupon the completion of energy delivery, the needle tip may be simply withdrawn from the subcutaneous tissue and skin such that the needle tract closes upon itself and prevents or inhibits any bleeding from the tissue. Moreover, the needle shaft may define one or more openings along a side surface of the shaft for directionally transmitting laser energy or heat energy via radiation or conduction through the one or more openings into the adjacent tissue. Because of the small size of the needle and optical fiber, no marks are left on the skin and no bleeding results, thus facilitating the procedure and eliminating any pain and time typically associated with such healing.

Electrical currents may also be conducted via the needle shaft and into the tissue region to be treated prior to or during treatment for stimulating any nerves which may be in the vicinity of the needle. If the muscle around the needle twitches, this may be an indication that nerves are proximate to the needle and treatment may be effected upon these nerves. If the muscle fails to twitch upon actuation of the electrical energy, this may be indication of the absence of nerves in the area and the needle may be withdrawn from the tissue and repositioned in another region where the process of nerve stimulation may be repeated for optimal treatment of the tissue.

Additionally, a fluid reservoir may also be provided which is in fluid communication with at least one needle. The fluid may be infused or injected through the needle into the tissue region prior to, during, or after applying laser energy. Examples of a fluid are anesthetics, analgesics, anti-inflammatory drugs, anti-histamines, non-steroidal drugs, steroidal drugs, anti-bacterial drugs, water, and saline. The fluid may also be an acid to facilitate tissue reduction and/or necrosis. The fluid may also be infused or injected through the needle to applying a cooling fluid into the tissue to minimize tissue injury to surrounding tissue regions.

BRIEF DESCRIPTION OF THE SEVERAL VIEWS OF THE DRAWINGS

FIG. 9 illustrates a detailed side view of a variation of a distal end of the device with a plurality of needles in a linear arrangement.

FIG. 10 illustrates a detailed end view of a variation of a distal end of the device with a plurality of needles in a grid arrangement.

FIG. 11 illustrations a partial cross-sectional view of tissue with the device of FIG. 5 advanced into fat.

DETAILED DESCRIPTION OF THE INVENTION

Figure 1:
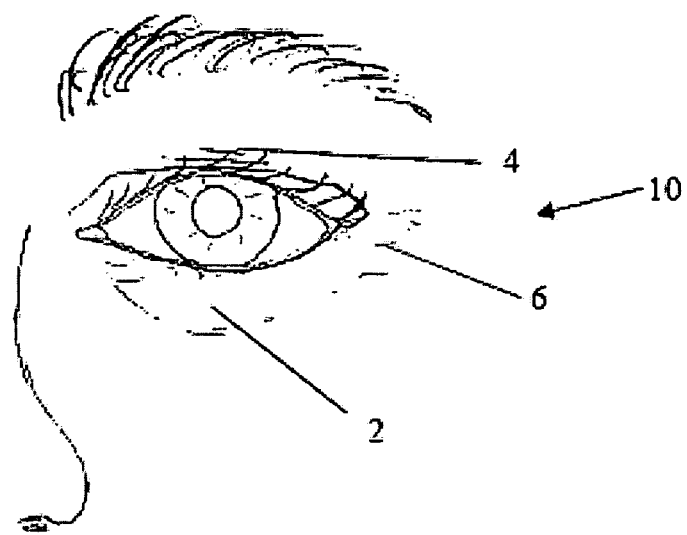
FIG. 1 illustrates a patient's eye with under eye bags and wrinkles.
Figure 2:
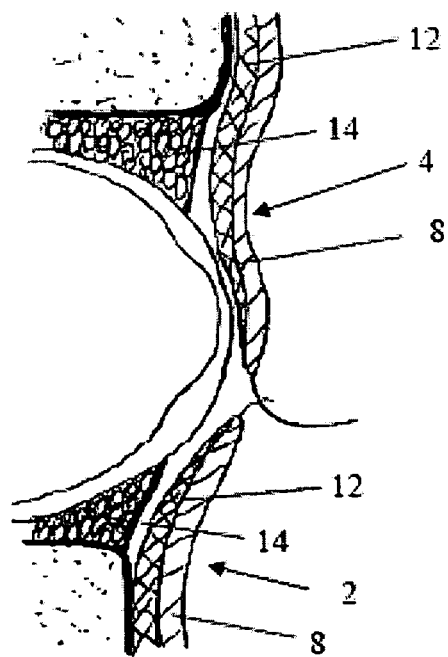
FIG. 2 shows a partial cross-sectional view of the anatomy of the eyelid

As illustrated in FIG. 1, lower eyelid bags 2, droopy upper eyelids 4, and/or eye wrinkles 6 may appear with age or because of other factors such as weight or sun damage. A youthful person normally has a strong support system for the eyelid structure, such elastic skin 8 and tight muscles 12, which hold back orbital fat 14, as shown in FIG. 2. As a person ages, skin 8 around the eye area 10 may begin to loose elasticity and muscles 12 may become lax resulting in bulging orbital fat 14, wrinkled 6 and/or baggy 2 skin. One method for reducing the signs of aging is to apply heat or energy (laser, radio frequency, ultrasound, etc.) to a target tissue region (fat, muscle, dermis, etc.) through an optical fiber within a lumen of or along a 20 to 30 gauge (or smaller) needle to cause tissue reduction and/or necrosis leading to a reduction of eye bags and/or wrinkles.

Although this and other examples may show the devices and methods described herein as utilized upon the facial region, this is intended to be illustrative and not limiting. Other regions of the body may, of course, be treated with such instruments and are also intended to be included within this description.

Figure 3:
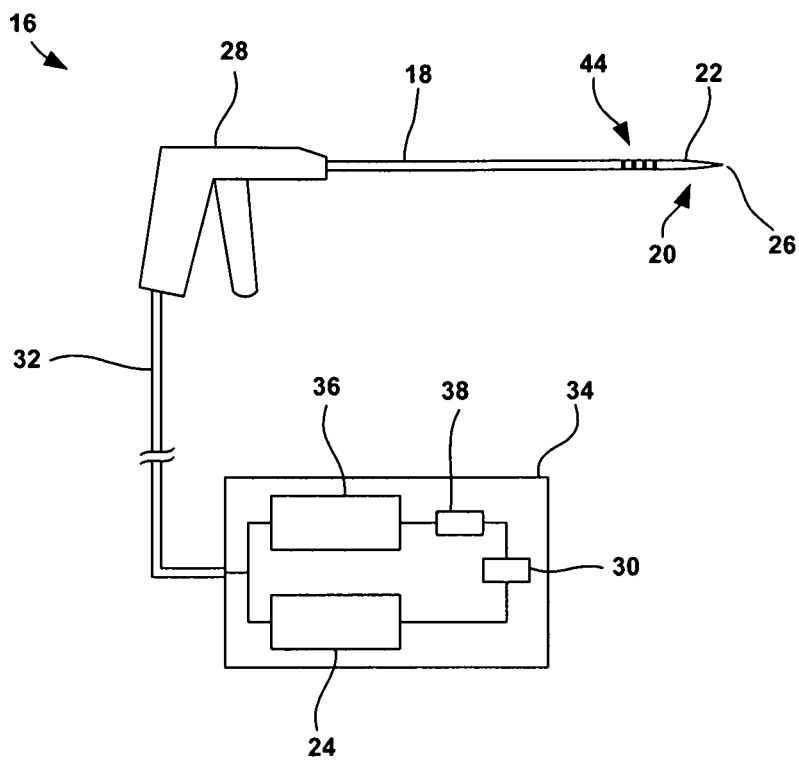
FIG. 3 shows a variation of a device used to deliver laser energy as well as for providing an infusion or injection of a fluid directly into tissue being treated.
Figure 7A:
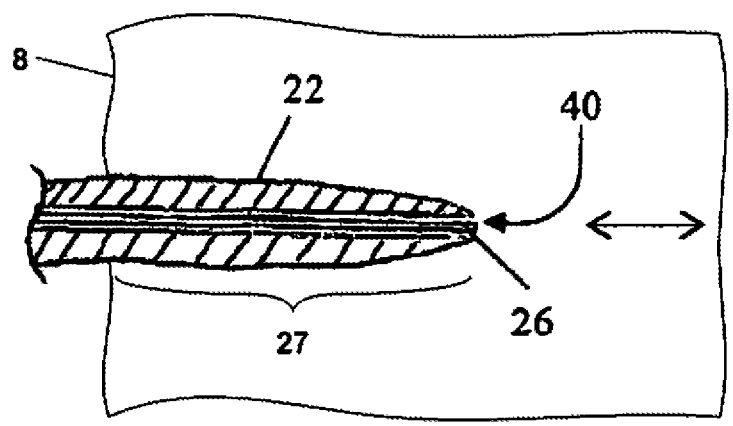
FIG. 7A shows a detail cross-sectional view of an advanceable needle defining a central lumen through which an optical fiber may be positioned.

FIG. 3 shows a variation of a device 16 to deliver laser energy as well as for providing an infusion or injection of a fluid directly into the tissue being treated by the laser energy. The device 16 is illustrated as having an elongate shaft 18 with a distal end portion 20 having at least one piercing tip, such as a needle 22 for piercing a patient's skin 8. The distal end portion 20 may be angled relative to the elongate shaft 18 or it may be straight depending upon the desired configuration. Moreover, the elongate shaft 18 and/or needle 22 may have one or more visual markings 44 or indicators along its length to indicate a depth of the shaft 18 and/or needle 22 into the tissue (e.g., treatment length 27 as shown in FIG. 7A) by comparison against the patient's skin surface.

The device 16 may include a laser generator 24 for delivering laser energy through the shaft 18 to the distal end portion 20, which is in optical communication with the proximal end of at least one optical fiber 26 positioned through the device 16 with the terminal end of the optical fiber 26 placed between or adjacent to the needle 22. The needle 22 may have a 20-30 gauge diameter (or smaller), preferably 27-30 gauge diameter, to avoid drawing of blood when puncturing skin 8 or the need for making an incision. The needle 22 may be made of a material, such as metal, which is designed to facilitate or limit heat transfer. The needle 22 may also contain slits or openings to assist with heat delivery.

Figure 4A:
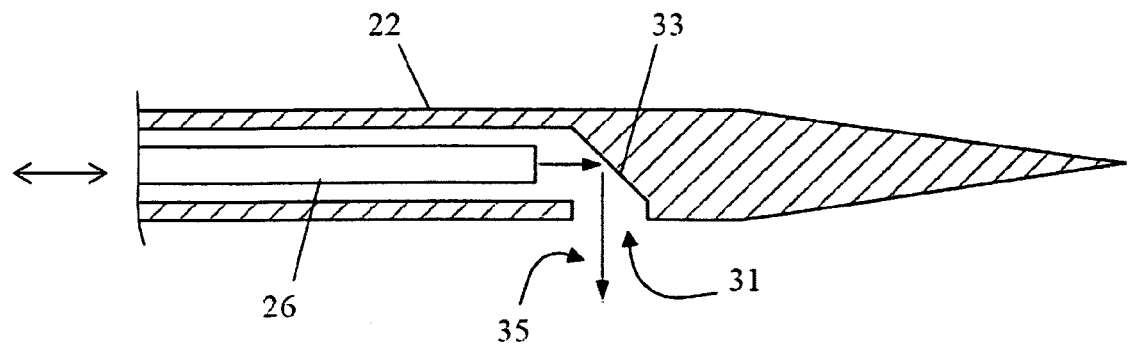
FIG. 4A shows a partial cross-sectional side view of a needle shaft having at least one opening defined along the shaft proximal to the needle tip.

For example, FIG. 4A illustrates a partial cross-sectional side view of a needle shaft 22 having at least one opening 31 defined along the shaft proximal to the needle tip. The opening 31 may be relatively small compared to the shaft circumference, e.g., ⅓ of the circumference, and may define any number of openings, e.g., circular, elliptical, rectangular, etc. The distal opening of the lumen defined through the needle 22 may be occluded or otherwise insulated and the opening 31 may be defined about, e.g., 2-3 mm proximal to the needle tip. An angled or beveled surface 33 may be defined adjacent to opening 31 within a terminal end of the lumen within shaft 22 proximal to the needle tip to direct the laser energy 35 emitted from the optical fiber 26 through opening 31 at an angle relative a longitudinal axis of needle shaft 22. In this manner, radiant laser energy 35 may be emitted through opening 31. Alternatively, angled or beveled surface 33 may be omitted and the distal opening of needle shaft 22 may be insulated or occluded such that the laser energy transmitted through the optical fiber 26 contacts and heats the distal tip. The resulting heat energy may be conducted or radiated through opening 31 rather than the laser energy itself.

Figure 4B:
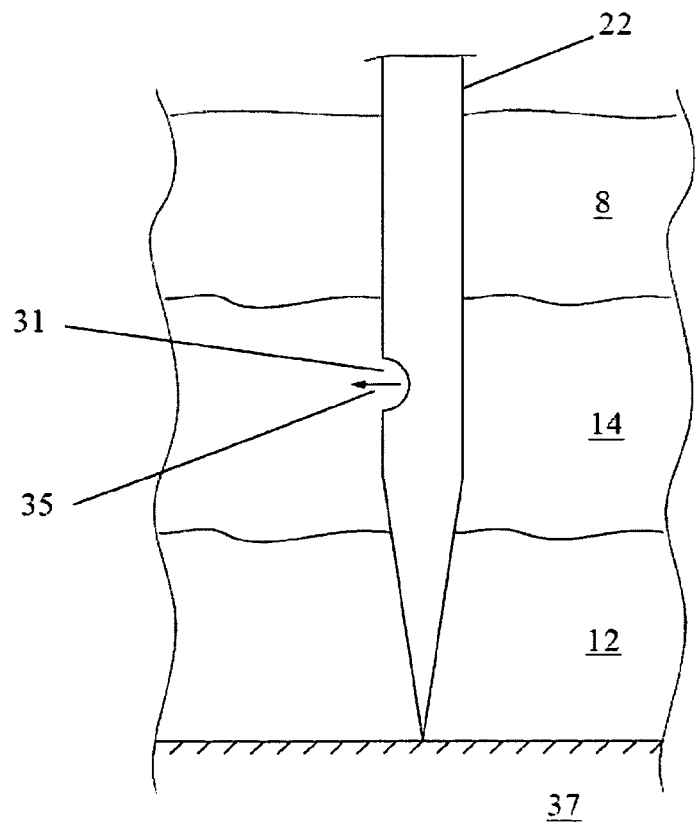
FIG. 4B illustrates a partial cross-sectional view of an example where the needle shaft is advanced through the skin surface such that the distal tip is placed directly against the surface of the underlying bone.
Figure 4C:
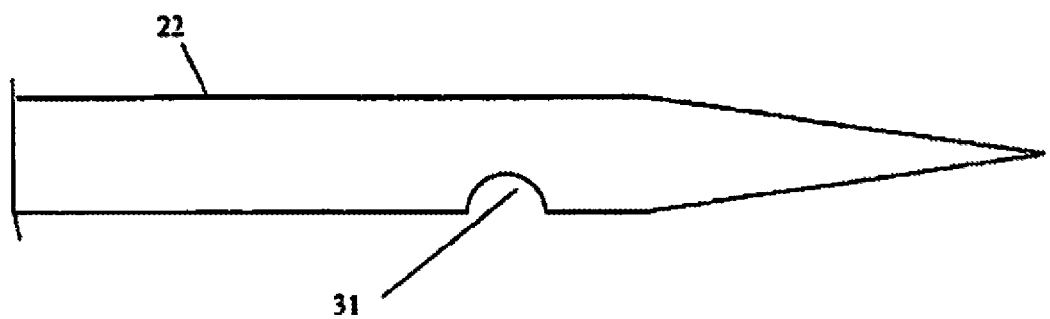
FIG. 4C shows a side view of a needle shaft defining a single opening proximal to its distal tip.
Figure 4D:
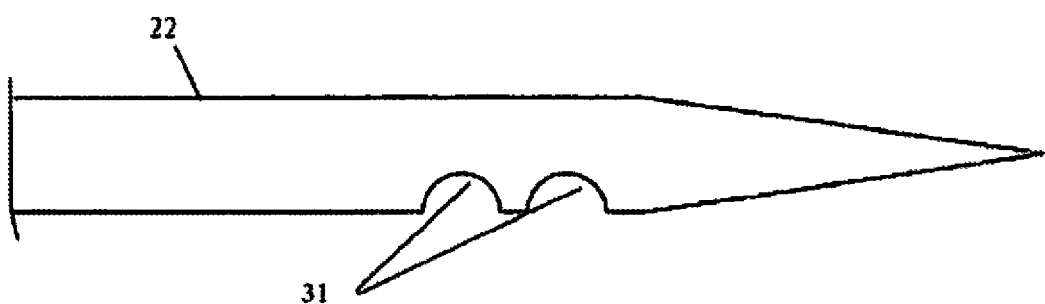
FIG. 4D shows a side view of another example of a needle shaft defining multiple openings proximal to its distal tip.

FIG. 4B illustrates a partial cross-sectional view of an example where needle shaft 22 is advanced through the skin surface 8, layer of fat 14, and layer of muscle 12 and the distal tip is placed directly against the surface of the underlying bone 37. Because of the placement of opening 31 along the shaft of needle 22 proximal to the tip, the redirected laser energy 35 (or otherwise radiated or conducted heat) may be passed through the opening 31 and into the fat 14 directly adjacent to the opening 31. The positioning of the opening 31 thus provides for precision heating through the shaft for directly treating the fat 14 beneath the skin 8. As previously mentioned, the needle shaft 22 may define a single opening 31 proximal to the needle tip, as shown in FIG. 4C. In other variations, multiple openings 31 may be defined along the shaft surface as practicable and as shown in FIG. 4D.

Figure 5:
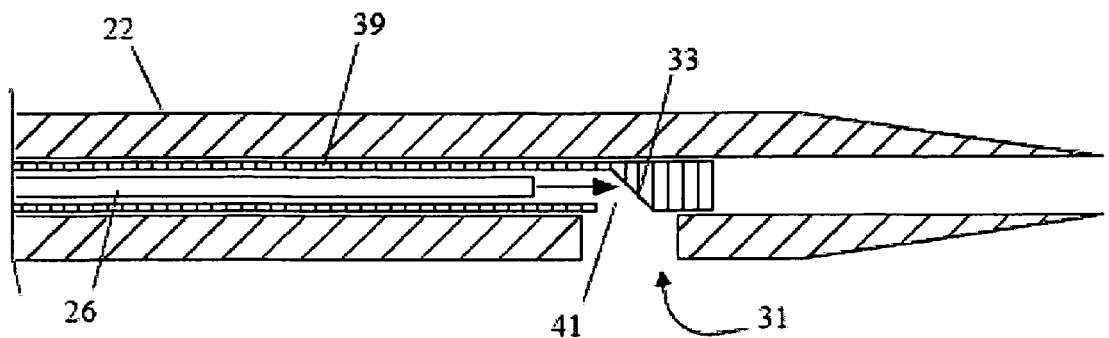
FIG. 5 illustrates a partial cross-sectional side view of a tubular shaft advanced through the lumen defined through the needle shaft.

In yet another variation, a tubular shaft 39 may be advanced through the lumen defined through the needle shaft 22, as shown in the partial cross-sectional view of FIG. 5. This shaft 39 may also define a lumen therethrough for advancing the optical fiber 26 within and it may also define a shaft opening 41 near or at a distal end of the shaft 39 optionally having an angled or beveled surface 33. Without use of tubular shaft 39, the optical fiber 26 may be simply advanced through the needle shaft 22 for transmitting the laser energy through a distal opening of the needle 22. However, with the placement of shaft 39 within the needle shaft 22 and the positioning of the optical fiber 26 within the shaft 39, the shaft opening 41 may be aligned with the opening 31 along the needle shaft 22 for energy transmission through the side opening.

Figure 6:
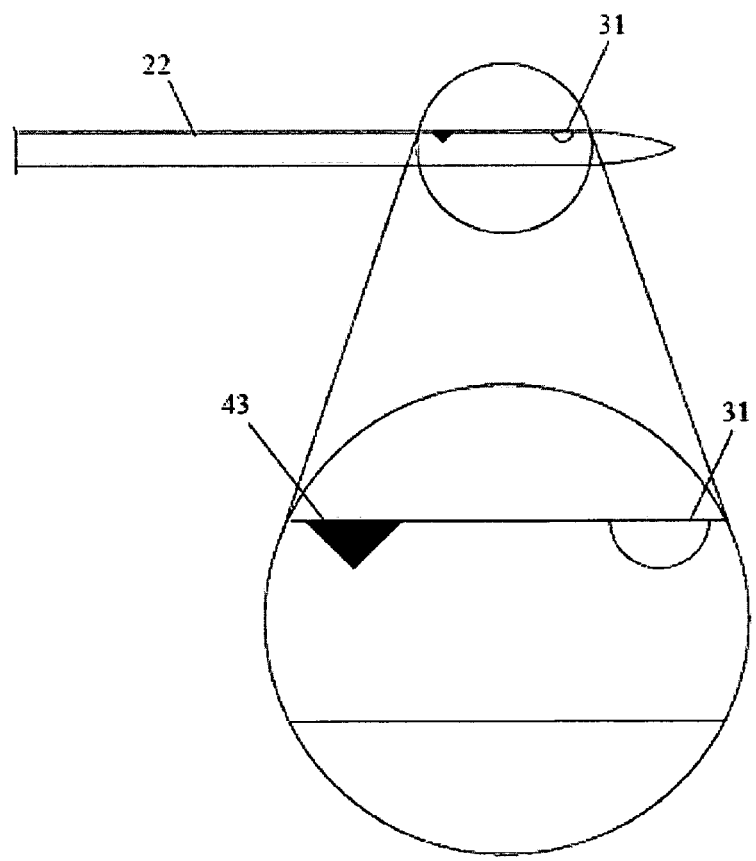
FIG. 6 illustrates side and detail side views of an example of a needle shaft having a marking or indicator placed along the shaft surface proximal to the opening.

When the needle shaft 22 has been advanced into the tissue, orientation of the opening 31 may be indicated, e.g., by a marking or indicator 43 placed along the needle shaft 22 proximal to the opening 31, as shown in the side and detail side views of FIG. 6. Indicator 43 may be aligned along the shaft body with the opening 31 such that when the needle has been inserted within the tissue, the indicator 43 remains visible to the user to indicate the directional orientation of the opening 31 within the tissue. In this manner, directional heating of the region beneath the skin surface may be accomplished by orienting the indicator 43, and thus the opening 31, in the desired direction of the tissue to be treated.

During treatment, a control or advancement mechanism on a handle 28, which is connected to a proximal end of shaft 18, may be actuated to advance the optical fiber 26 at least partially beyond the distal end of the needle 20 into the target tissue region. The optical fiber 26 may be extended as far as needed to reach the target tissue. For example, the optical fiber 26 may be extended 3 mm from the distal end of the needle when the needle 22 is inserted at approximately a 90° angle relative to the treatment area (direct frontal insertion). The optical fiber 26 may extend further if the needle 22 is inserted into the patient's skin from the side or at an angle. To avoid the optical fiber 26 being inserted beyond the target region, the fiber 26 may be curved or the length may be limited.

After insertion of the needle 20 into the target tissue region, the laser generator 24 may be actuated to deliver laser energy through the terminal end of the optical fiber 26. The laser may be configured as any number of laser instruments. For instance the laser generator 24 may be an Argon laser or $CO_2$ laser capable of inducing temperatures of, e.g., of 750° to 900° C., to vaporize the underlying tissue. Moreover, a controller or central processor 30 may be configured to control the laser generator 24 to deliver pulsed laser energy through the terminal end of the optical fiber 26 for a controlled period of time and frequency.

Fluid may be injected and/or infused into the tissue region to serve a number of different purposes. One purpose is to bulk up the physical size of the tissue by injecting the fluid to present a larger surface area to be treated. The enlarged surface area may help to ensure that the laser energy is properly delivered directly into the intended tissue rather than surrounding tissues. Examples of fluids which may be used for bulking tissue may include any number of suitable fluids, e.g., saline, water, etc. Moreover, acids such as salicylic acid or glycolic acid may also be injected into tissue to assist with causing tissue reduction, necrosis, scarring, and/or sclerosis.

Another purpose is for drug delivery directly into the treated tissue. For instance, anesthetic fluids or other fluids infused with analgesics (e.g., lidocaine with or without epinephrine, marcaine with or without epinephrine, etc.) may be injected into the tissue to provide for pain management during and after the application of the laswer energy. Additionally, other drugs for injection may include any number of medications, such as steroidal drugs (e.g., corticosteroids, dexamethasone, beclomethasone, etc.), non-steroidal drugs (e.g., non-steroidal anti-inflammatory drugs, etc.), anti-inflammatory drugs, anti-histamines (e.g., diphenhydramine, etc.), anti-bacterial drugs, etc. which may be injected to control excessive post treatment swelling as well as infection.

Accordingly, the device 16 may also include an electronic/fluid cable 32 which is electrically and fluidly connected to the handle 28 and is further connected to a power/infusion assembly 34. Within the assembly 34 is a fluid reservoir 36 and a pump 38 electrically coupled to a central processor 30. Any of the above-mentioned fluids, e.g., analgesics, anesthetics, anti-inflammatory drugs, water, saline, etc., may be filled within reservoir 36 for delivery through the cable 32, elongate shaft 18 and through the needles 22 for delivery into the tissue. The infusion rate of the fluid and control of the pump 38 may be determined by the controller 30. An example of a pump which is pre-programmed to inject a fluid in a controlled injection rate and which may be utilized with the pump 38 is commercially available as the CompuDent® delivery system and Wand® handpiece (Milestone Scientific, Inc., South Orange Livingston, N.J.).

In passing the optical fiber 26 through the needle body, the fiber 26 may be independently translatable within a needle lumen 40. In this variation, the fiber 26 may be passed through the same lumen 40 utilized for fluid infusion through the needle, if fluid infusion is utilized. Alternatively, the optical fiber 26 may be affixed within the lumen 40 of the needle such that advancement or retraction of the needle also likewise advances or retracts the optical fiber 26 relative to the elongate shaft 18. Moreover, the optical fiber 26 in either case may be configured (if affixed) or otherwise urged (if translatable) to extend just proximal to, adjacent with, or distally beyond the lumen opening or needle tip and into the tissue 8 during treatment to alter a treatment length 27 of the shaft 18, as shown in FIG. 7A.

FIG. 7A illustrates one variation of the optical fiber 26 positioned within the lumen 40 of the needle 22 in the partial cross-sectional detail view. The optical fiber 26 may be optionally translatable relative to the needle 22, as indicated by the arrow, and positioned centrally through the needle 22 such that the distal tip of the optical fiber 26 is extendable through the distal tip of the needle 22.

Figure 7B:
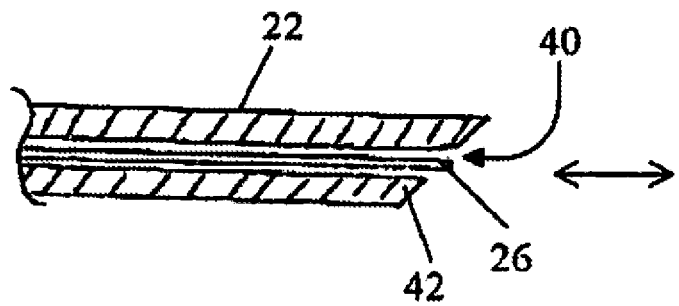
FIG. 7B shows a detail cross-sectional view of another variation where a lumen opening may terminate along a surface of the needle proximal to a piercing tip.

FIG. 7B illustrates another variation where the optical fiber 26 may be optionally translatable, as indicated by the arrow, relative to the needle 22 which defines an angled piercing surface 42. The optical fiber 26 may exit the lumen 40 opening at a location along a side surface of the needle 22 proximal to the piercing tip so as not to inhibit entry of the needle 22 into the tissue to be treated.

Figure 7C:
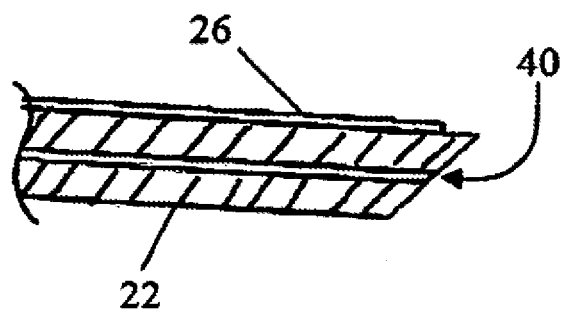
FIG. 7C shows yet another variation where the optical fiber may be positioned along an outer surface of the piercing needle.

FIG. 7C illustrates yet another variation where the optical fiber 26 may be optionally placed or integrated along an outer surface of the needle 22 leaving the lumen 40 open for fluid infusion. The optical fiber 26 may be adhered or affixed to the needle 22 via any number of mechanisms, e.g., adhesives, outer sheath, etc., or otherwise integrated with the body of the needle 22. Alternatively, the infusion of fluids may be omitted entirely and the optical fiber 26 may be advanced through the needle 22 after or simultaneously with the needle 22 when projected from the shaft 18 into the tissue to be treated.

Figure 8:
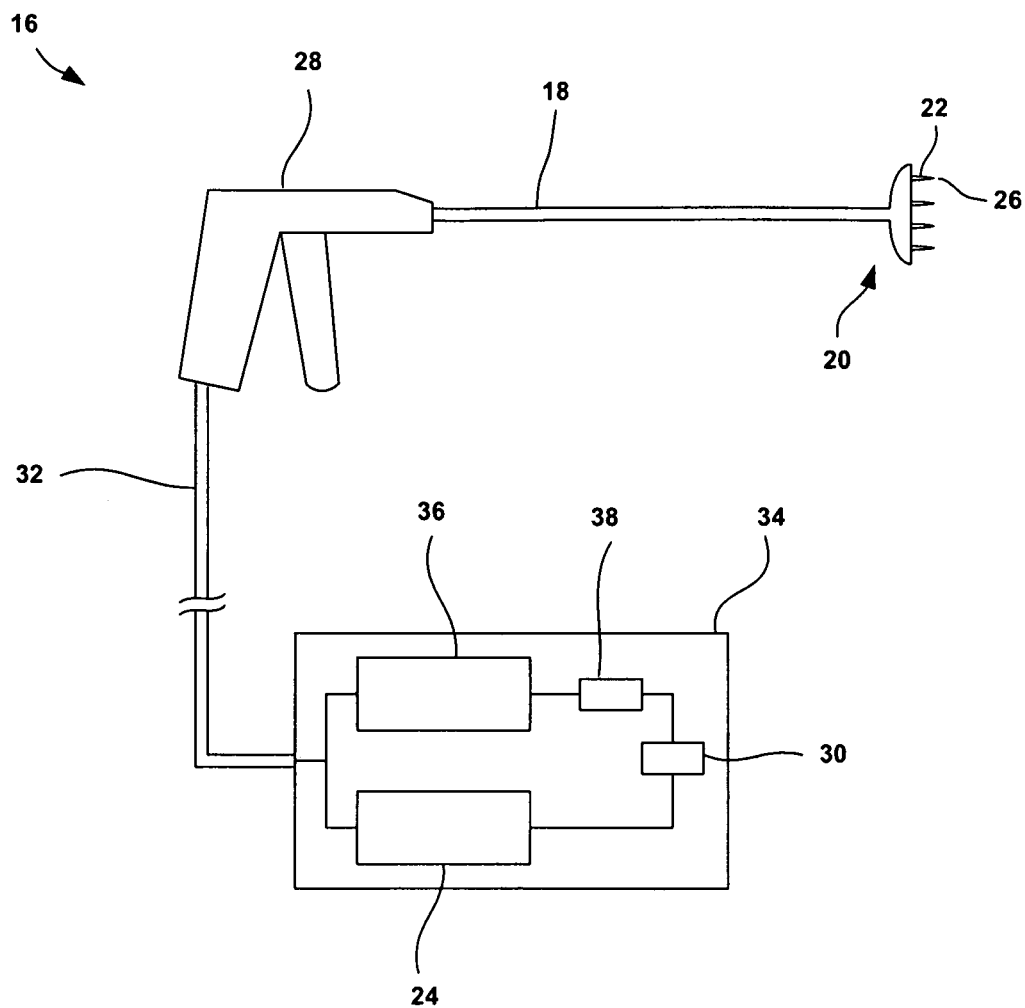
FIG. 8 shows another variation of the device used to deliver laser energy as well as for providing an infusion or injection of a fluid directly into the tissue through a plurality of needles.

Another variation of the device 16 is illustrated in FIGS. 8-10. The distal end portion 20 of the elongate shaft 18 may alternatively include a structure 70 that contains more than one needle 22 to affect a broad surface of tissue. FIGS. 9-10 illustrate the structure 70 containing needles 22 arranged in a grid-like pattern, however any configuration, such a linear, curved, circular, random, etc. may be used. Each needle 22 may be the same gauge or length as other needles on the structure 70 or they may be different or a combination. The Each needle 22 may also contain an optical fiber 26 or be used for fluid delivery, however selective use of each needle 22 may be regulated by the controller 30, depending on treatment strategy and/or the target tissue. Depending on the length of each needle 22 on the structure 70, multiple target tissue regions, such as fat 14 or muscle 12, may be treated at the same time. To avoid inserting the needles 22 too far into the tissue, a surface of the structure adjacent to the proximal end of the needles 72 may make contact with the patient's skin, limiting further insertion of the needles 22, as illustrated in FIG. 11.

Other examples of a laser delivery device may be found in U.S. patent application Ser. No. 11/750,873 filed May 18, 2007, the content of which is hereby incorporated by reference in its entirety.

Figure 12:
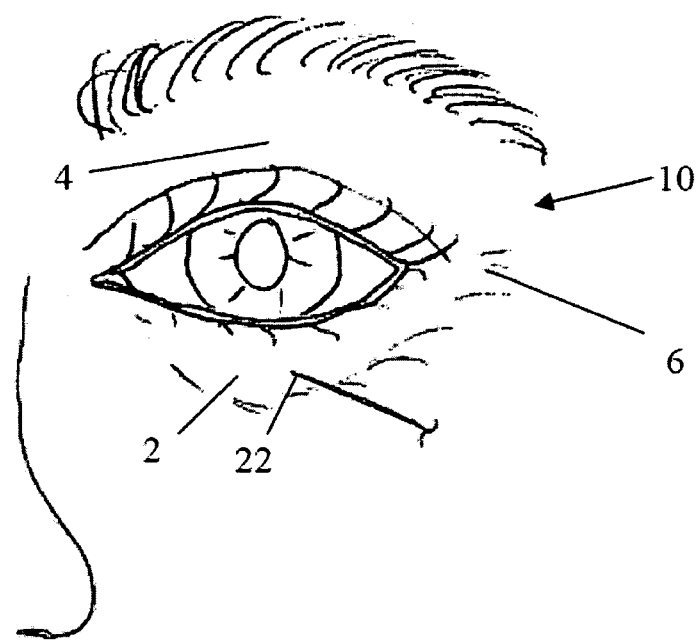
FIG. 12 illustrates the device advanced into the lower eye lid region.
Figure 13:
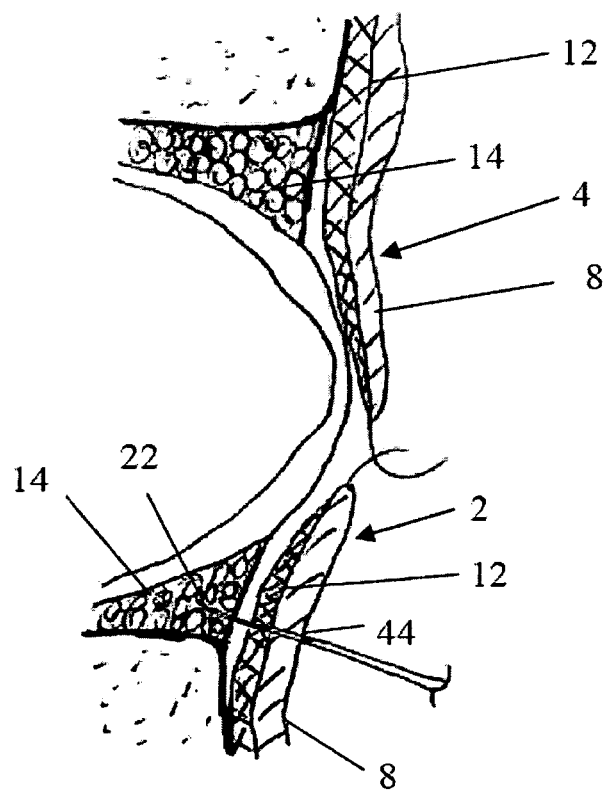
FIG. 13 shows a partial cross-sectional view of the eyelid with the device advanced into orbital fat.
Figure 14A:
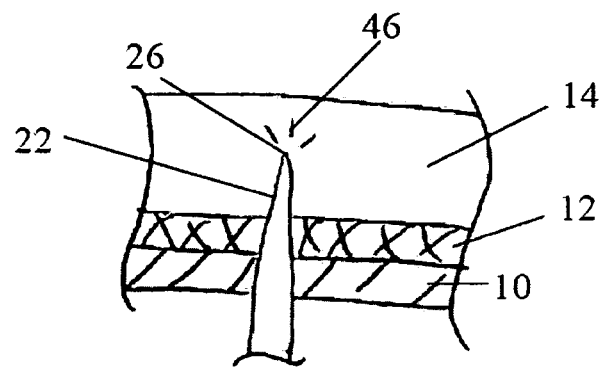
FIGS. 14A to 14C illustrate one method in which an infusion needle may be advanced into the tissue to be treated to infuse a fluid and then an optical fiber may be advanced through the needle to treat the region of tissue via laser energy.

In an exemplary method of use, one or more needles 22 (a single needle is shown for illustrative purposes only and is not intended to be limiting) located at the distal end of the device 16 may be advanced through the skin of the lower eyelid 2 into a target tissue region to be treated, e.g., fat 14, as shown in FIGS. 12-13. As illustrated by FIG. 14A, once the needle 22 is desirably positioned, fluid 46 may be optionally infused into the fatty tissue 14, as described above, and the optical fiber 26 may be advanced through the needle 22. Alternatively, the optical fiber 26 may be advanced into the fatty tissue 14 simultaneously with the needle 22 and infusion of the tissue may be omitted.

Figure 14B:
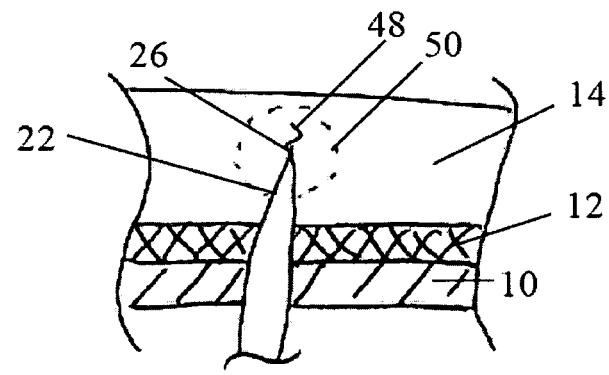

With the optical fiber 26 positioned proximate to or within the fatty tissue 14, laser energy 48 may be passed through the optical fiber 26, as described above, to ablate the tissue region around the needle 50, as shown in FIG. 14B. Laser energy 48 may be used to heat the fatty tissue 14 directly or may also be used to heat the needle 22 which in turn may heat the fatty tissue 14. Fat absorption may be increased using certain wavelengths. For example, a laser frequency of 600-1200 nm may be used when heating the needle 22. A frequency of 900-1500 nm or 1400-1900 may also be used when heating the fatty tissue 14 and the needle 22.

Figure 14C:
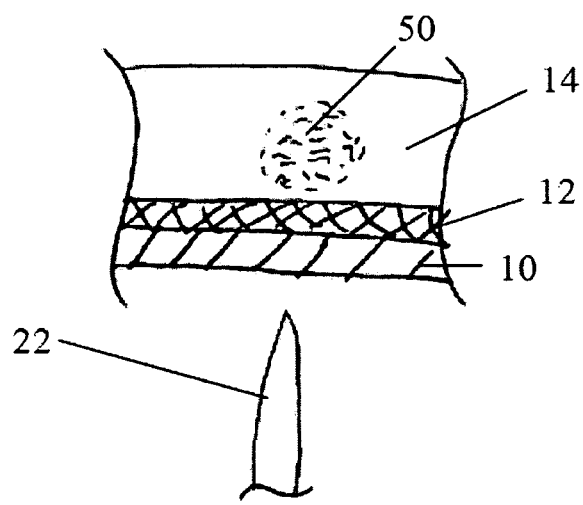

Once the treatment has been completed, the needle 22 and the optical fiber 26 may be retracted or withdrawn and repositioned to another tissue region or withdrawn entirely from the patient body, as shown in FIG. 14C, and the ablated fatty tissue may be re-absorbed through the patient's lymphatic system and phagocytes. As described above, because of the small diameter of the piercing needle tip (e.g., 20 to 30 gauge or smaller), the needle 22 and optical fiber 26 may be inserted directly into and through the patient's skin without the need for any surgical incision or intervention. With the completion of energy delivery, the needle 22 may be simply withdrawn from the subcutaneous tissue and skin such that the needle tract closes upon itself and prevents or inhibits any bleeding from the tissue. Because of the small size of the needle 22 and optical fiber 26, no marks are left on the skin and no bleeding results, thus facilitating the procedure and eliminating any pain. If bleeding does occur as a result of the needle 22, any such bleeding may be minimized as a result of the reduced size of the needle 22 and no further procedure may be needed to stop the bleeding, for instance, because of the relatively small size of the puncture, no stitches or other interventions may be required.

Figure 15:
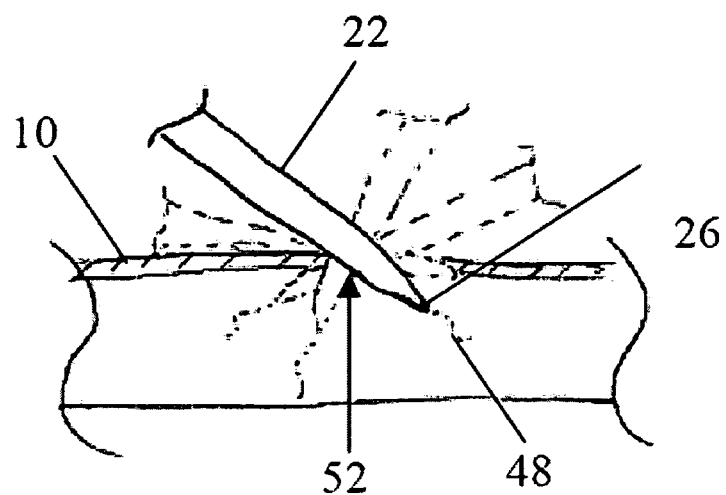
FIG. 15 illustrates advancement of the device into tissue at a plurality of angles through a single puncture site.
Figure 16:
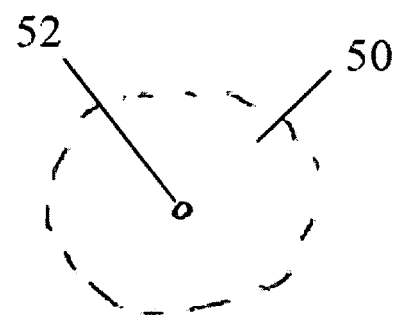
FIG. 16 illustrates the lesion zone created by the advancement method of FIG. 12.

Alternatively, as shown in FIGS. 15-16, the needle 22 may be inserted within the same puncture site 52 (1×1 mm or 2×2 mm, etc.) by altering the insertion angle within the puncture site, e.g. laterally. Multiple insertions through the same puncture site 52 may result in a broader lesion or ablation region 50. The device 16 may include a gauge to limit the angle or depth of the needle 22.

Figure 17:
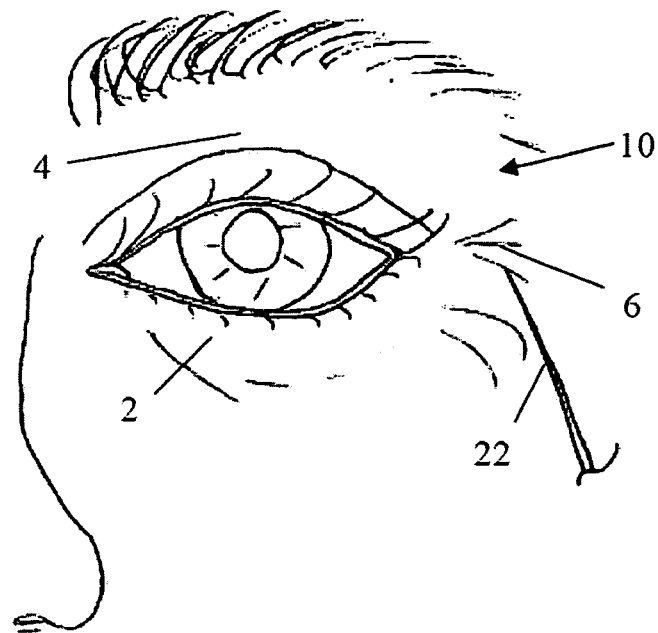
FIG. 17 illustrates the device advanced into a wrinkle in the outer eye region.
Figure 18:
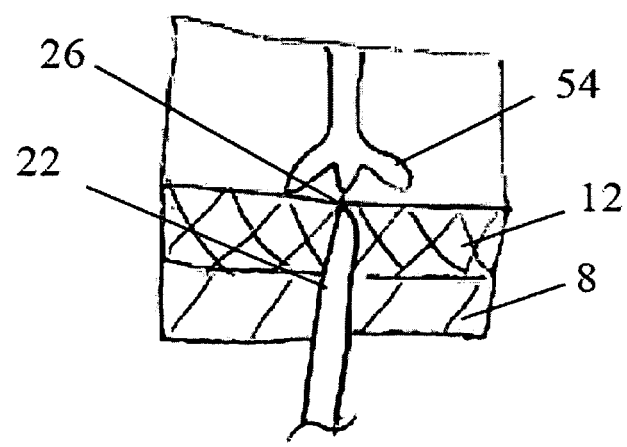
FIG. 18 shows a partial cross-sectional view of tissue with the device advanced into a nerve.

In addition to fat, other tissue regions may also be treated using laser energy. For example, prominent forehead creases, brow furrows or eye lines 6 produced by specific facial expression muscles repeatedly creasing the skin 8 may be effectively treated by reducing the function of specific facial muscles 12. As shown in representative FIGS. 17-18, the needle 22 may be passed under the skin 8 along the path of muscles 12 and nerves or nerve endings 54 wherein laser energy 48 may be applied, innervating the muscles 12. When nerves 54 and/or muscles 12 are injured by the laser energy 48 the muscle action is reduced, thus reducing wrinkles. There may also be small amounts of heat transfer to the dermis or layers of the skin which may also cause skin tightening, further reducing wrinkles. The pattern of heat disbursement may be regulated by the controller 30 so as to create lateral heat delivery.

One method for determining whether a nerve or nerve endings are in proximity to the needle prior to or during treatment is to electrically stimulate any nerves in proximity to the needle. The needle may be advanced into the tissue region to be treated and prior to emitting laser energy into the tissue, a low intensity electrical current may be transmitted through the needle shaft, e.g., at a current level of 1 mA or lower such as 0.2 mA. The electrical current may stimulate any local nerves to contract and twitch the underlying muscles giving an indication to the user that a nerve or nerves are in proximity to the needle tip and that treatment may proceed in that particular tissue region without having to withdraw the needle shaft 22 from the tissue. If twitching is absent, this may be an indication that nerves are absent from the tissue region and the needle may be withdrawn from the tissue and repositioned at another location where the nerve stimulation process may be repeated.

Figure 19A:
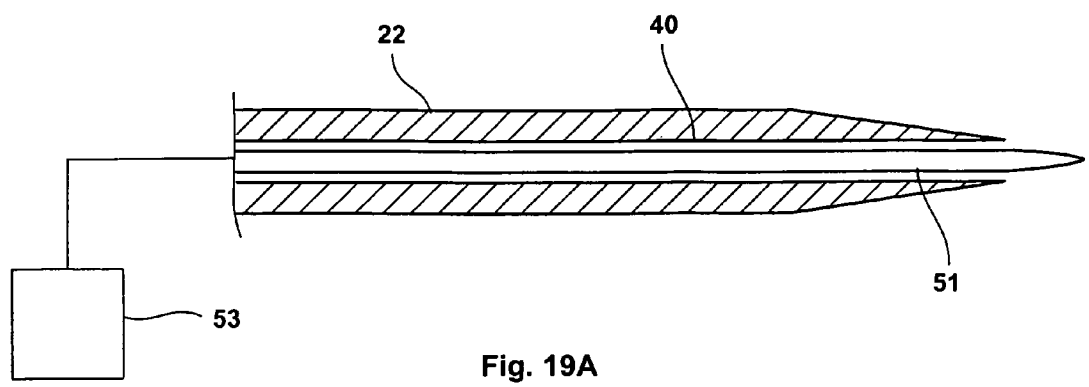
FIGS. 19A to 19C illustrate partial cross-sectional side views of variations of needle shafts incorporating a nerve stimulation device.

An example of a device which may be used to transmit the electrical current for nerve detection is shown in the partial cross-sectional side view in FIG. 19A. In this example, a separate conductive shaft 51 coupled to a power supply 53 may be advanced within lumen 40 defined through needle shaft 22. The distal tip of the conductive shaft 51 may be introduced through the skin and into the tissue via needle 22 where the electrical current may be conducted into any adjacent nerves. If a nerve or nerves are located, as indicated by the resulting twitching, the physician may remove the conductive shaft 51 from the lumen 40 and introduce the optical fiber 26 through lumen 40 and into proximity with the tissue to be treated without removing or readjusting a position of the needle 22 relative to the tissue.

Figure 19B:
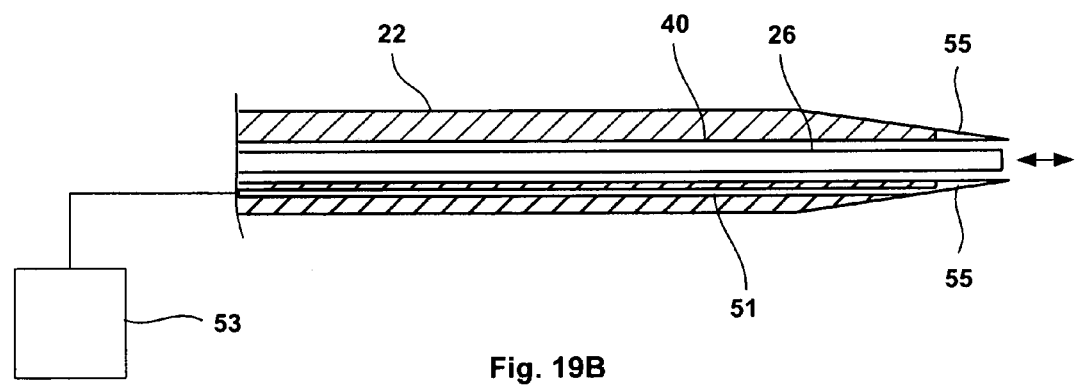
Figure 19C:
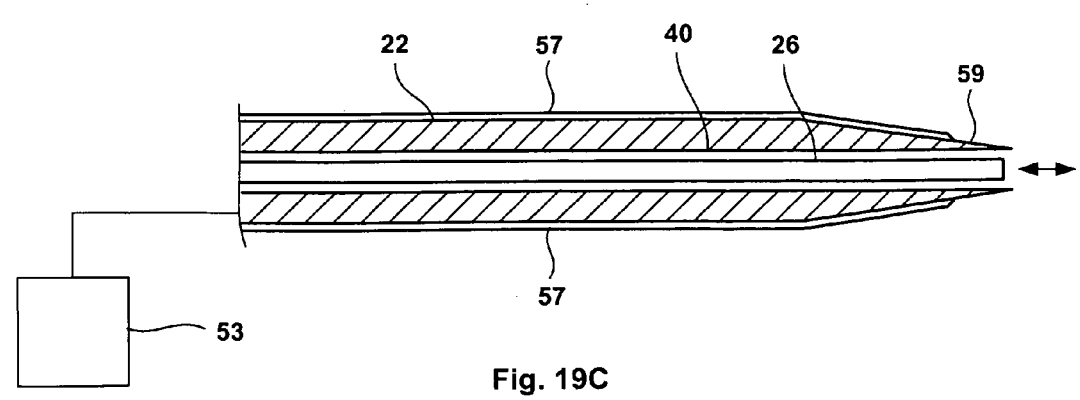

Another example is illustrated in the partial cross-sectional side view of FIG. 19B, which shows a variation where a conductive tip 55 may be integrated with the distal tip of needle 22. Conductive tip 55 may be attached to the needle 22 and electrically coupled via conductive shaft 51 which may be integrated through needle shaft 22 and electrically coupled to the power supply 53. With conductive tip 55 integrated with the needle 22, electrical stimulation of any nerves may be conducted without having to utilize a separate nerve stimulation instrument. With the lumen 40 clear, optical fiber 26 may be positioned within and tissue treatment may be initiated immediately upon the underlying tissue.

In yet another variation, electrical current may be conducted directly through the needle shaft 22 itself, provided that the needle is fabricated from an electrically conductive material. An insulating cover 57 may be placed over the body of needle shaft 22 with the insulation terminating proximal to the distal tip of the needle 22 such that an exposed tip 59 remains in contact with the tissue. The electrical current may thus be conducted through the exposed tip 59 to determine the presence of any nerves without having to remove the optical fiber 26 from the lumen 40.

Additionally and/or alternatively, rather than utilizing the conductive tip 55 or the exposed electrode tip 59 to detect for the presence of a nerve in proximity to the electrode, the conducted current may be increased and the needle 22 itself may be used to ablate the subcutaneous tissue surrounding the needle 22. The electrode may be configured as a monopolar (or bipolar) electrode assembly and the electrical energy may be used to supplement the laser treatment or used independently of the laser treatment.

Figure 20:
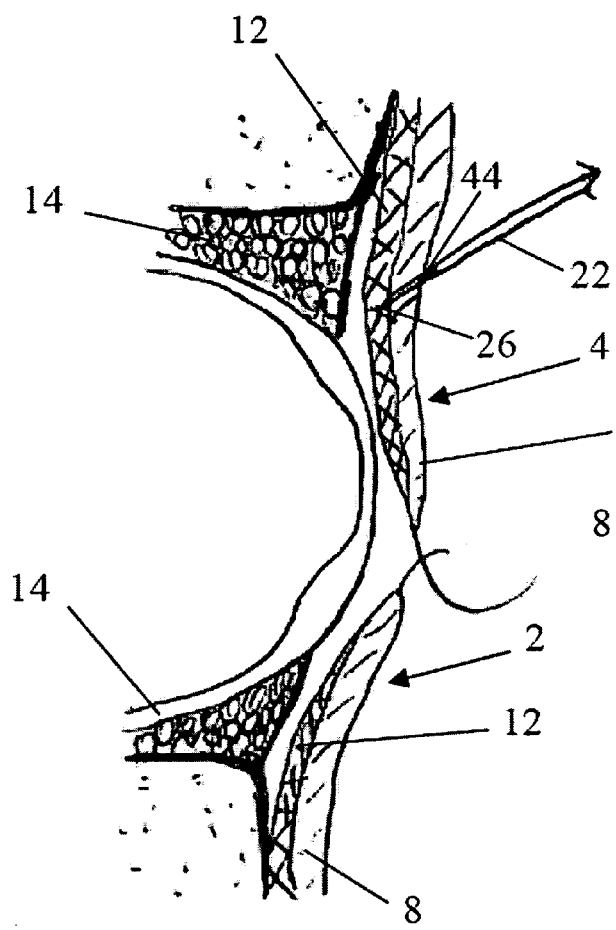
FIG. 20 shows a partial cross-sectional view of the eyelid with the device advanced into muscle.

Laser energy 48 may also be applied to muscle 12 to induce tissue reduction. As shown in FIG. 20, the needle 22 may be inserted through the upper eyelid 4 into the muscle 12. The optical fiber 26 may be advanced to apply laser energy 48 causing tissue reduction in the muscle 12 which may result in the upper eyelid 4 being lifted upward toward the brow area, therefore reducing the appearance of a droopy upper eyelid 4.

Figures 21, 22:
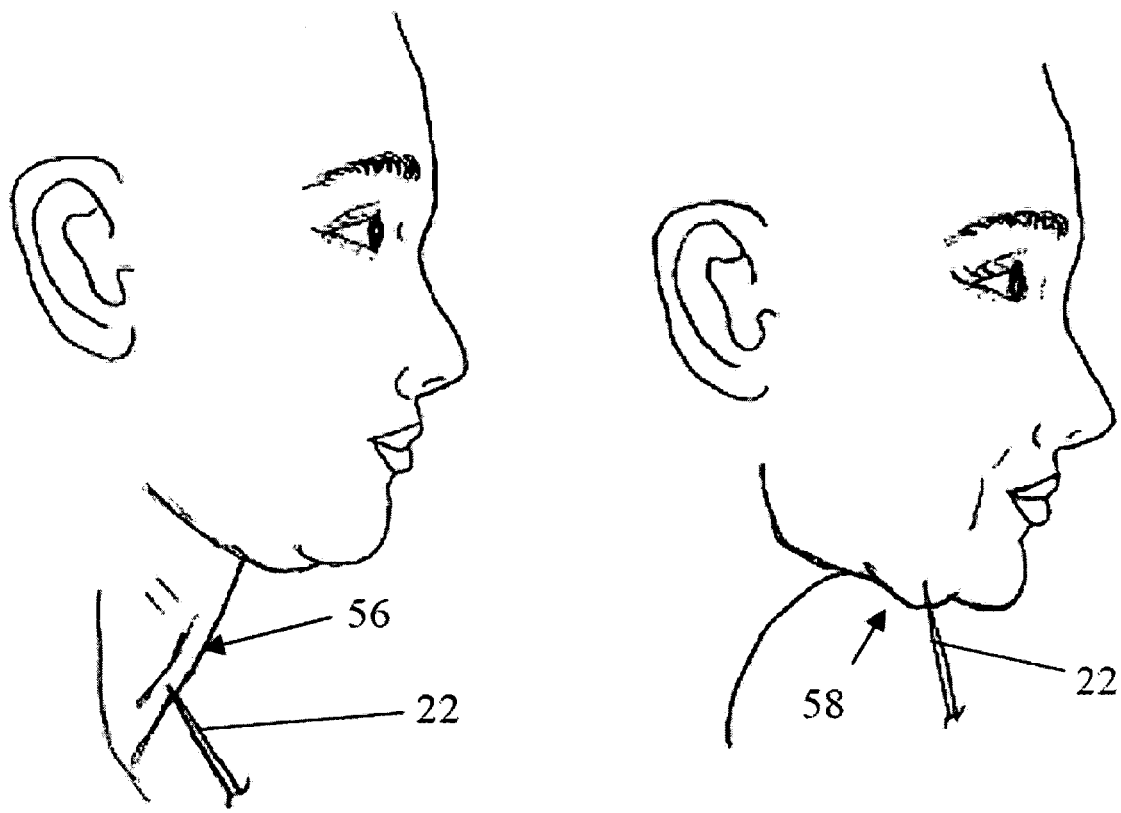
FIG. 21 illustrates the device advanced into neck.
FIG. 22 illustrates the device advanced into the jowl.

In alternative methods of use, other areas of the patient's body may be treated in a manner similar to those described above. An example is illustrated in FIG. 21 where the needle 22 may be inserted in the platysmal or neck area 56 into a subcutaneous target tissue region (fat, muscle, etc.) to reduce the appearance of bulging fat and/or sagging skin. Another example is illustrated in FIG. 22 where the needle 22 may be inserted in the cheek area 58 to reduce the appearance of unsightly jowls.

Figure 23:
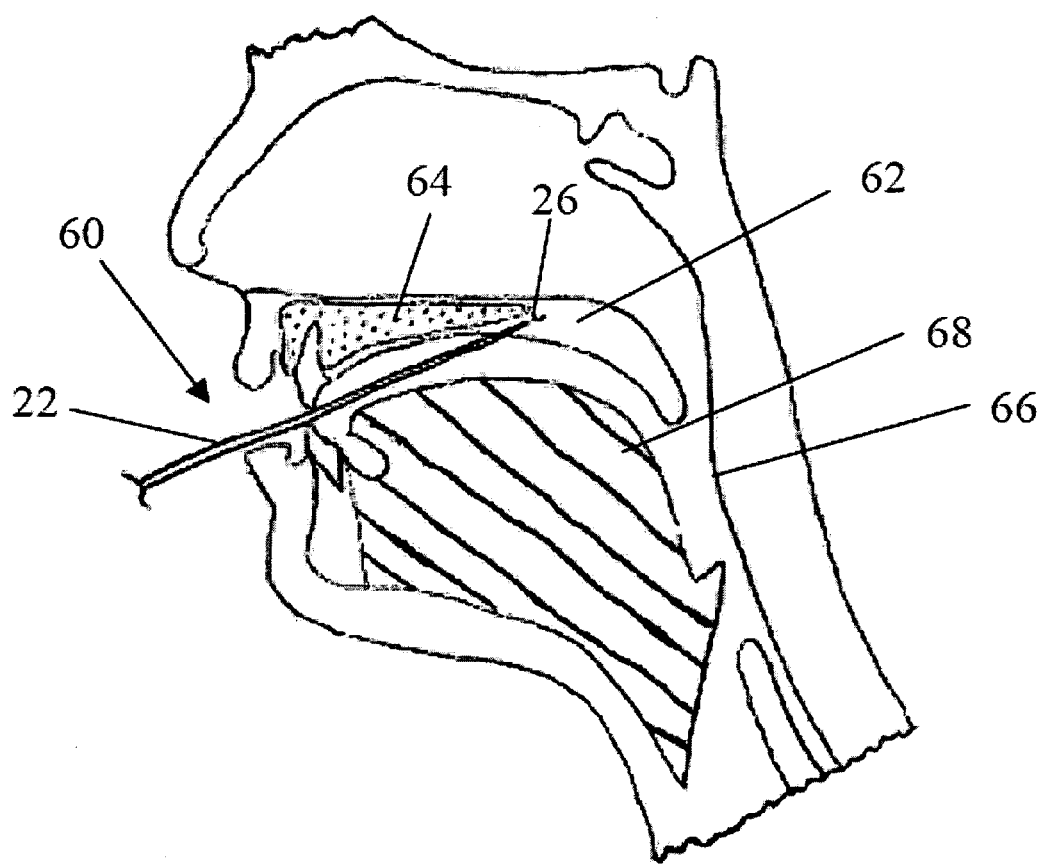
FIG. 23 shows a partial cross-sectional view of the oral cavity with the device advanced into the soft palate.

Yet another example is illustrated in FIG. 23 where the elongate shaft 18 may be advanced into the patient's mouth 60 and the one or more needles 22 may be advanced inferiorly (anterior to posterior) into the soft palate 62 adjacent to the hard palate 64. Optical fibers 26 may be utilized to ablate the tissue region within or around the soft palate 62. The optical fiber 26 may be inserted at various depths, e.g. 2 mm, 3 mm, etc., to treat a broad range of tissue. In another example, the elongate shaft 18 may also be advanced further into the patient's mouth 60 to treat areas in or around the pharyngeal tissue 66 or in or around the base of the tongue 68. Ablating tissue in the soft palate 62, pharyngeal tissue 66, and/or the base of the tongue 68 may result in altering the mass and/or stiffness of the tissue which may reduce the vibration level and in turn decrease the intensity of snoring. Snoring occurs when air fails to flow smoothly through the nose or the mouth 60 and/or when the soft tissues or muscles in the air passages vibrate at some resonant frequency.

The applications of the devices and methods discussed above are not limited to the treatment of the tissue regions in or around the facial area or for cosmetic purposes but may include any number of further treatment applications. Other treatment sites may include areas or regions of the body. Modification of the above-described device and methods for carrying out the invention, and variations of aspects of the invention that are obvious to those of skill in the art are intended to be within the scope of the claims.

What is claimed is:

1. A method of reducing eye bags and/or wrinkles, comprising:
   inserting an elongated shaft having at least one piercing tip having between a 20 and 30 gauge diameter into an eyelid of a subject and into a tissue region of interest comprising fat underlying the skin surface such that bleeding is inhibited from the skin surface and tissue region surrounding the piercing tip;

advancing a terminal end of at least one optical fiber into the tissue region of interest within or along the piercing tip;

altering a position of the terminal end of the optical fiber relative to the piercing tip while the piercing tip remains stationary such that the piercing tip is positioned proximate to the tissue region of interest;

conducting an electrical current along the elongate shaft towards the piercing tip and into the tissue region and monitoring for a presence of twitching of the tissue region as an indication of a nerve being in proximity to the elongate shaft; and, if twitching of the tissue region is observed, applying laser energy controlled via a controller to deliver pulsed laser energy having a wavelength of between 600 to 1900 nm for a controlled period of time such that at least some of the laser energy from the optical fiber impinges upon and heats the shaft such that tissue reduction and/or necrosis is induced in the fat within the tissue region.

2. The method of claim 1 wherein inserting comprises multiple insertions through a single insertion site at a plurality of angles relative to the tissue region.

3. The method of claim 1 further comprising inserting a plurality of piercing tips.

4. The method of claim 3 wherein the piercing tips are the same gauge relative to one another.

5. The method of claim 3 wherein the piercing tips are different gauges relative to one another.

6. The method of claim 1 wherein the tissue region comprises orbital fat.

7. The method of claim 1 wherein the tissue region further comprises muscle.

8. The method of claim 1 wherein the tissue region further comprises a nerve.

9. The method of claim 1 further comprising infusing or injecting a fluid through at least one needle into the tissue region prior to, during, or after applying laser energy.

10. The method of claim 9 wherein the fluid is selected from the group consisting of anesthetics, analgesics, anti-inflammatory drugs, anti-histamines, non-steroidal drugs, steroidal drugs, anti-bacterial drugs, water, and saline.

11. The method of claim 9 wherein the fluid is an acid.

12. The method of claim 9 further comprising applying a cooling fluid into the tissue region.

13. The method of claim 1 wherein conducting an electrical current comprises conducting electrical current of 1 mA or lower.

14. The method of claim 1 further comprising directionally transmitting energy through one or more openings defined along a shaft proximal to the piercing tip.

* * * * *